(12) United States Patent
Mulligan et al.

(10) Patent No.: US 6,664,112 B2
(45) Date of Patent: Dec. 16, 2003

(54) METHODS FOR IMPROVING THE SEQUENCE FIDELITY OF SYNTHETIC DOUBLE-STRANDED OLIGONUCLEOTIDES

(75) Inventors: John T. Mulligan, Seattle, WA (US); John C. Tabone, Bothell, WA (US)

(73) Assignee: Blue Heron Biotechnology, Inc., Bothell, WA (US)

( * ) Notice: Subject to any disclaimer, the term of this patent is extended or adjusted under 35 U.S.C. 154(b) by 0 days.

(21) Appl. No.: 09/872,761

(22) Filed: Jun. 1, 2001

(65) Prior Publication Data

US 2002/0077471 A1 Jun. 20, 2002

Related U.S. Application Data

(60) Provisional application No. 60/208,753, filed on Jun. 2, 2000.

(51) Int. Cl.[7] .......................... G01N 33/00; C12Q 1/68; C12P 19/34; C07H 21/02; C07H 21/04
(52) U.S. Cl. .............................. 436/94; 435/6; 435/91.1; 536/23.1; 536/24.3; 536/24.33
(58) Field of Search ........................... 435/6, 91.1, 183, 435/287.2; 436/94; 536/23.1, 24.3, 24.33; 422/68.1, 50

(56) References Cited

U.S. PATENT DOCUMENTS

| | | | | |
|---|---|---|---|---|
| 4,652,639 A | | 3/1987 | Stabinsky | 536/27 |
| 5,668,268 A | * | 9/1997 | Tang et al. | 536/25.3 |
| 5,770,714 A | * | 6/1998 | Agabian et al. | 536/23.1 |
| 5,795,976 A | | 8/1998 | Oefner et al. | 536/25.4 |
| 5,942,609 A | | 8/1999 | Hunkapiller et al. | 536/25.3 |

FOREIGN PATENT DOCUMENTS

WO   WO 99/23257   5/1999

OTHER PUBLICATIONS

Huber et al., Detection of partial denaturation in AT–rich DNA fragments by ion–pair reversed–phase chromatography. Anal. Chem., 68, 2959–2965, 1996.*

Huang and Krugh, "Large–Scale Purification of Synthetic Oligonucleotides and Carcinogen–Modified Oligodeoxynucleotides on a Reverse–Phase Polystyrene (PRP–1) Column," *Analytical Biochemistry* 190(1):21–25, Oct. 1990.

O'Donovan et al., "Blind Analysis of Denaturing High–Performance Liquid Chromatography as a Tool for Mutation Detection," *Genomics* 52(1):44–49, Aug. 15, 1998.

Hecker et al., "Optimization of Cloning Efficacy by Pre–Cloning DNA Fragment Analysis," *Biotechniques* 26(2):216–218, Feb. 1999.

Hecker and Kobayashi "Sequencing of DNA Fragments Isolated with the WAVE Nucleic Acid Fragment Analysis System," Application Note 115, Transgenomic, Inc., 2000.

Huber,"Micropelicular Stationary Phases for High–performance Liquid Chromatography of Double–Stranded DNA," *J. of Chromatography A.* 806:3–30, 1998.

Lehming et al., "Recognition Helices of lac and λ Repressor are Oriented in Opposite Directions and Recognize Similar DNA Sequences," *PNAS U.S.A.* 85(21):7947–7951, Nov. 1988.

Lehming et al., "The Interaction of the Recognition Helix of lac Repressor with lac Operator," *The EMBO Journal* 6(10):3145–3153, Oct. 1987.

Markiewicz et al., "Genetic Studies of the lac Repressor XIV. Analysis of 4000 Altered *Escherichia coli* lac Repressors Reveals Essential and Non–essential Residues, as well as "Spacers" which do not Require a Specific Sequence," *J. of Molecular Biology* 240(5):421–433, Jul. 29, 1994.

Shaw–Bruha and Lamb, "Ion Pair–Reversed Phase HPLC Approach Facilitates Subcloning of PCR Products and Screening of Recombinant Colonies," *BioTechniques* 28(4):794–797, Apr. 2000.

Suckow et al., "Genetic Studies of the Lac Repressor XV:4000 Single Amino Acid Substitutions and Analysis of the Resulting Phenotypes on the Basis of the Protein Structure,"*J. Mol. Biol.* 261:509–523, 1996.

* cited by examiner

*Primary Examiner*—Ethan Whisenant
*Assistant Examiner*—Frank Wei Min Lu
(74) *Attorney, Agent, or Firm*—Seed Intellectual Property Law Group PLLC

(57) ABSTRACT

Synthetic oligonucleotides, such as synthetic DNA, often contain sequence errors due to synthetic failures (e.g., side products and/or truncated products). Methods are provided herein for improving the sequence fidelity of synthetic double-stranded oligonucleotides by separative depletion of synthetic failures. Separation is effected by utilization of methodologies in a preparative mode under denaturing conditions. A preferred use of the methods relates to gene synthesis.

12 Claims, No Drawings

SEQUENCE LISTING

<160> NUMBER OF SEQ ID NOS: 15

<210> SEQ ID NO 1
<211> LENGTH: 205
<212> TYPE: DNA
<213> ORGANISM: Artificial Sequence
<220> FEATURE:
<223> OTHER INFORMATION: 205 base pair segment of the lacI gene sequence
      synthesized using overlapping double-stranded
      oligonucleotides

<400> SEQUENCE: 1
aattcataaa ggagatatca tatgaaaccg gtaacgttat acgacgtcgc tgaatacgcc    60
ggcgtttctt accagaccgt ttctagagtg gttaaccagg cttcacatgt tagcgctaaa   120
acccgggaaa aagttgaagc tgccatggct gagctcaact acatcccgaa ccgtgttgcg   180
cagcagctgg ctggtaaaca aagct                                        205

<210> SEQ ID NO 2
<211> LENGTH: 25
<212> TYPE: DNA
<213> ORGANISM: Artificial Sequence
<220> FEATURE:
<223> OTHER INFORMATION: Modified oligonucleotides containing 2,6
      diaminopurine
<220> FEATURE:
<221> NAME/KEY: modified_base
<222> LOCATION: (11)...(11)
<223> OTHER INFORMATION: n = 2,6-diaminopurine

<400> SEQUENCE: 2
accgtttcta nagtggttaa ccagg                                         25

<210> SEQ ID NO 3
<211> LENGTH: 25
<212> TYPE: DNA
<213> ORGANISM: Artificial Sequence
<220> FEATURE:
<223> OTHER INFORMATION: Modified oligonucleotides containing 2,6
      diaminopurine
<220> FEATURE:
<221> NAME/KEY: modified_base
<222> LOCATION: (13)...(13)
<223> OTHER INFORMATION: n = 2,6-diaminopurine

<400> SEQUENCE: 3
accgtttcta gantggttaa ccagg                                         25

<210> SEQ ID NO 4
<211> LENGTH: 25
<212> TYPE: DNA
<213> ORGANISM: Artificial Sequence
<220> FEATURE:
<223> OTHER INFORMATION: Modified oligonucleotides containing 2,6
      diaminopurine
<220> FEATURE:
<221> NAME/KEY: modified_base
<222> LOCATION: (8)...(8)
<223> OTHER INFORMATION: n = 2,6-diaminopurine

<400> SEQUENCE: 4
ggaaaaantt gaagctgcca tggct                                         25

<210> SEQ ID NO 5
<211> LENGTH: 26
<212> TYPE: DNA

```
<213> ORGANISM: Artificial Sequence
<220> FEATURE:
<223> OTHER INFORMATION: Modified oligonucleotides containing 2,6
      diaminopurine
<220> FEATURE:
<221> NAME/KEY: modified_base
<222> LOCATION: (3)...(3)
<223> OTHER INFORMATION: n = 2,6-diaminopurine

<400> SEQUENCE: 5
ttncgcagca gctggctggt aaacaa                                          26

<210> SEQ ID NO 6
<211> LENGTH: 25
<212> TYPE: DNA
<213> ORGANISM: Artificial Sequence
<220> FEATURE:
<223> OTHER INFORMATION: Modified nucleotides containing uracil.

<400> SEQUENCE: 6
tgaagcctgg ttaaccactu tagaa                                           25

<210> SEQ ID NO 7
<211> LENGTH: 25
<212> TYPE: DNA
<213> ORGANISM: Artificial Sequence
<220> FEATURE:
<223> OTHER INFORMATION: Modified nucleotides containing uracil.

<400> SEQUENCE: 7
agctcagcca tggcagcttc aautt                                           25

<210> SEQ ID NO 8
<211> LENGTH: 25
<212> TYPE: DNA
<213> ORGANISM: Artificial Sequence
<220> FEATURE:
<223> OTHER INFORMATION: Modified nucleotides in which uracil was
      substituted for adenosine.

<400> SEQUENCE: 8
agctcagcca tggcagcttc auctt                                           25

<210> SEQ ID NO 9
<211> LENGTH: 26
<212> TYPE: DNA
<213> ORGANISM: Artificial Sequence
<220> FEATURE:
<223> OTHER INFORMATION: Modified nucleotides in which uracil was
      substituted for adenosine.

<400> SEQUENCE: 9
ttgcgcugca gctggctggt aaacaa                                          26

<210> SEQ ID NO 10
<211> LENGTH: 197
<212> TYPE: DNA
<213> ORGANISM: Artificial Sequence
<220> FEATURE:
<223> OTHER INFORMATION: Fragment of the lacI gene sequence.

<400> SEQUENCE: 10
cataaaggag atatcatatg aaaccggtaa cgttatacga cgtcgctgaa tacgccggcg     60
tttcttacca gaccgtttct agagtggtta accaggcttc acatgttagc gctaaaaccc    120
gggaaaaagt tgaagctgcc atggctgagc tcaactacat cccgaaccgt gttgcgcagc    180
```

```
agctggctgg taaacaa                                                       197

<210> SEQ ID NO 11
<211> LENGTH: 48
<212> TYPE: DNA
<213> ORGANISM: Artificial Sequence
<220> FEATURE:
<223> OTHER INFORMATION: Control synthetic 48 bp sequence

<400> SEQUENCE: 11
attcgccctt tgccactaag caccagcgaa acggtactta ccgacacg                      48

<210> SEQ ID NO 12
<211> LENGTH: 47
<212> TYPE: DNA
<213> ORGANISM: Artificial Sequence
<220> FEATURE:
<223> OTHER INFORMATION: 48mer containing synthesis byproducts

<400> SEQUENCE: 12
attcgccctt tgccactaag caccagcgaa acggtactac cgacacg                       47

<210> SEQ ID NO 13
<211> LENGTH: 49
<212> TYPE: DNA
<213> ORGANISM: Artificial Sequence
<220> FEATURE:
<223> OTHER INFORMATION: 48mer containing synthesis byproducts

<400> SEQUENCE: 13
attcgccctt tgccactaag caccagcgaa acggtactttt accgacacg                     49

<210> SEQ ID NO 14
<211> LENGTH: 48
<212> TYPE: DNA
<213> ORGANISM: Artificial Sequence
<220> FEATURE:
<223> OTHER INFORMATION: 48mer containing synthesis byproducts

<400> SEQUENCE: 14
attcgccctt tgccactaag caccagcgaa acggtacttg ccgacacg                      48

<210> SEQ ID NO 15
<211> LENGTH: 48
<212> TYPE: DNA
<213> ORGANISM: Artificial Sequence
<220> FEATURE:
<223> OTHER INFORMATION: 48mer containing synthesis byproducts

<400> SEQUENCE: 15
attcgccctt tgccactaag caccagcgaa acggtactta gcgacacg                      48
```

METHODS FOR IMPROVING THE SEQUENCE FIDELITY OF SYNTHETIC DOUBLE-STRANDED OLIGONUCLEOTIDES

CROSS-REFERENCE TO RELATED APPLICATION

This application claims the benefit of U.S. Provisional Patent Application No. 60/208,753 filed Jun. 2, 2000, where this provisional application is incorporated herein by reference in its entirety.

TECHNICAL FIELD

The present invention is generally directed toward improving the sequence fidelity of synthetic double-stranded oligonucleotides. It is more particularly related to the removal of synthetic failures (including side products and truncated products) created in the synthesis of oligonucleotides, such as double-stranded DNA.

BACKGROUND OF THE INVENTION

Much of the discovery research in pharmaceutical companies is focused on genes, either as targets for drug development or as therapeutics in the form of their protein expression products. These companies have access to a majority of the human genes. Pharmaceutical companies are overwhelmed with potential opportunities, acutely aware that their competitors are looking at the same set of possibilities, and currently unable to work on more than a fraction of the genes that have been identified. One of the major bottlenecks in this research is the time and effort required to prepare genes for detailed analysis.

Gene synthesis, the production of cloned genes partially or entirely from chemically synthesized DNA, is one method of overcoming this bottleneck. In principle, gene synthesis can provide rapid access to any gene for which the sequence is known and to any variation on a gene. Reliable, cost-effective automated gene synthesis would have a revolutionary effect on the process of biomedical research by speeding up the manipulation and analysis of new genes.

One principal factor limiting the automation of gene synthesis is the low sequence fidelity of the process: gene clones created from chemically synthesized DNA often contain sequence errors. These errors can be introduced at many stages of the process: during chemical synthesis of the component oligonucleotides, during enzymatic assembly of the double-stranded oligonucleotides, and by chemical damage occurring during the manipulation and isolation of the DNA or during the cloning process.

Four types of base modifications are commonly produced when an oligonucleotide is synthesized using the phosphoramidite method: (1) Transamination of the O6-oxygen of deoxyguanosine to form a 2,6-diaminopurine residue; (2) Deamination of the N4-amine of deoxycytidine to form a uridine residue (Eadie, J. S. and Davidson, D. S., Nucleic Acids Res. 15:8333, 1987); (3) Depurination of N6-benzoyldeoxyadenosine yielding an apurinic site (Shaller, H. and Khorana, H. G., J. Am. Chem. Soc. 85:3828, 1963; Matteucci, M. D. and Caruthers, M. H., J. Am. Chem. Soc. 103:3185, 1981); (4) Incomplete removal of the N2-isobutyrlamide protecting group on deoxyguanosine. Each of these side products (byproducts) can contribute to sequence errors in cloned synthetic DNA.

Another synthetic failure of oligonucleotide synthesis is the formation of truncated products that are less than the full length of the desired oligonucleotide. The solid phase approach to oligonucleotide synthesis involves building an oligomer chain that is anchored to a solid support through its 3'-hydroxyl group, and is elongated by coupling to its 5'-hydroxyl group. The yield of each coupling step in a given chain-elongation cycle will generally be<100%. For an oligonucleotide of length 'n', there are n−1 linkages and the maximum yield of a desired coupling will be [coupling efficiency]$^{n-1}$. For a 25-mer, assuming a coupling efficiency of 98%, the calculated yield of full-length product will be 61%. The other 39% consists of all possible shorter length oligonucleotides (truncated products) resulting from inefficient monomer coupling. The desired oligonucleotide can be partially purified from this mixture by purification steps using ion exchange or reverse phase chromatography. These purification procedures are not 100% effective and do not completely eliminate these populations. The final product therefore contains n−1 and to some extent n−2 and n−3 failure sequences. This type of undesired product of the oligonucleotide synthesis process can also contribute to sequence errors in synthetic genes.

Another class of synthetic failures is the formation of "n+" products that are longer than the full length of the desired oligonucleotide (User Bulletin 13, 1987, Applied Biosystems). The primary source of these products is branching of the growing oligonucleotide, in which a phosphoramidite monomer reacts through the bases, especially the N-6 of adenosine and the O-6 of guanosine. Another source of n+ products is the initiation and propagation from unwanted reactive sites on the solid support. Finally, these products also form if the 5'-trityl protecting group is inadvertently deprotected during the coupling step. This premature exposure of the 5'-hydroxyl allows for a double addition of a phosphoramidite. This type of synthetic failure of the oligonucleotide synthesis process can also contribute to sequence errors in synthetic genes.

Another process common to the preparation of synthetic genes is the ligation of synthetic double-stranded oligonucleotides to other synthetic double-stranded oligonucleotides to form larger synthetic double-stranded oligonucleotides. In vitro experiments have shown that T4 DNA ligase exhibits poor fidelity, sealing nicks with 3' and 5' A/A or T/T mismatches (Wu, D. Y., and Wallace, R. B., Gene 76:245–54, 1989), 5' G/T mismatches (Harada, K. and Orgel, L. Nucleic Acids Res. 21:2287–91, 1993) or 3' C/A, C/T, T/G, T/T, T/C, A/C, G/G or G/T mismatches (Landegren, U., Kaiser, R., Sanders, J., and Hood, L., Science 241:1077–80, 1988). These types of mismatches may occur during ligation of double-stranded nucleic acids into larger double-stranded nucleic acids.

Due to the difficulties in the current approaches to the preparation of oligonucleotides, such as genes, there is a need in the art for methods for improving the sequence fidelity of synthetic oligonucleotides. The present invention fills this need, and further provides other related advantages.

SUMMARY OF THE INVENTION

Briefly stated, the present invention provides a variety of methods for improving the sequence fidelity of synthetic double-stranded oligonucleotides. The methods comprise subjecting synthetic double-stranded oligonucleotides to preparative column chromatography or preparative gel chromatography under denaturing conditions sufficient to separate the synthetic double-stranded oligonucleotides into two populations, wherein one population is enriched for synthetic failures and the other population is depleted of synthetic failures. In one embodiment, the column chromatography is HPLC. A preferred embodiment is DHPLC. In another embodiment, the gel chromatography is gradient gel chromatography. In any of the embodiments, the oligonucleotides may comprise synthetic double-stranded DNA. Preferred synthetic double-stranded DNA comprises one or more fragments of a larger DNA molecule.

These and other aspects of the present invention will become evident upon reference to the following detailed description. In addition, various references are set forth herein. Each of these references is incorporated herein by reference in its entirety as if each was individually noted for incorporation.

DETAILED DESCRIPTION OF THE INVENTION

Prior to setting forth the invention, it may be helpful to an understanding thereof to set forth definitions of certain terms to be used hereinafter.

Natural bases of DNA—adenine (A), guanine (G), cytosine (C) and thymine (T). In RNA, thymine is replaced by uracil (U).

Synthetic double-stranded oligonucleotides—substantially double-stranded DNA composed of single strands of oligonucleotides produced by chemical synthesis or by the ligation of synthetic double-stranded oligonucleotides to other synthetic double-stranded oligonucleotides to form larger synthetic double-stranded oligonucleotides.

Synthetic failures—undesired products of oligonucleotide synthesis; such as side products, truncated products or products from incorrect ligation.

Side products—chemical byproducts of oligonucleotide synthesis.

Truncated products—all possible shorter than the desired length oligonucleotide, e.g., resulting from inefficient monomer coupling during synthesis of oligonucleotides.

TE—an aqueous solution of 10 mM Tris and 1 mM EDTA, at a pH of 8.0.

Homoduplex oligonucleotides—double-stranded oligonucleotides wherein the bases are fully matched; e.g., for DNA, each A is paired with a T, and each C is paired with a G.

Heteroduplex oligonucleotides—double-stranded oligonucleotides wherein the bases are mispaired, i.e., there are one or more mismatched bases; e.g., for DNA, an A is paired with a C, G or A, or a C is paired with a C, T or A, etc.

The present invention is directed toward methods that provide for double-stranded oligonucleotides with a reduced sequence error rate from a mixture of synthetic oligonucleotides. The methods are based on the use of techniques in a preparative mode under conditions sufficient to separate double-stranded oligonucleotides which contain synthetic failures (including side products and truncated products) from the desired length double-stranded oligonucleotides that contain completely matched natural bases.

More specifically, the disclosure of the present invention shows surprisingly that a population of synthetic double-stranded oligonucleotides can be separated into two populations by methodologies when utilized in a preparative mode under denaturing conditions. One population is enriched for oligonucleotides containing synthetic failures (e.g., side products, products from incorrect ligation and/or truncated products). A second population is depleted of oligonucleotides containing synthetic failures and is enriched for synthetic double-stranded oligonucleotides of a desired length which contain only matched natural bases.

Depletion of synthetic failures from the desired double-stranded oligonucleotides refers generally to at least about a two-fold depletion relative to the total population prior to separation. Typically, the depletion will be a change of about two-fold to three-fold from the original state. The particular fold depletion may be the result of a single separation or the cumulative result of a plurality of separations. The second population is useful, for example, where the oligonucleotides are double-stranded DNA which correspond to a gene or fragments of a gene.

As disclosed herein, synthetic molecules containing natural bases can be separated from those containing synthetic failures, e.g., unnatural bases or truncated sequences. Unnatural bases in double-stranded oligonucleotides, like mismatched bases of heteroduplexed oligonucleotides, destabilize the double-stranded oligonucleotides. Double-stranded oligonucleotides (such as double-stranded DNA) containing unnatural bases or being less than full length, melt at a lower temperature than sequences of full length containing only natural bases in a homoduplex. By adjusting the temperature, double-stranded synthetic oligonucleotide failures will melt or partially melt, and migrate differently on chromatography than synthetic homoduplex oligonucleotides of full length. Thus, various methodologies, such as column chromatography or gel chromatography, can be used in a preparative manner under denaturing conditions to separate synthetic failures from the desired synthetic double-stranded oligonucleotides.

Oligonucleotide synthesis (e.g., chemical synthesis) can generate a variety of side products. For example, side products include an abasic residue (e.g., an apurinic or apyrimidinic residue), diaminopurine, an incompletely deprotected G, and uridine. For purposes of the present invention, the common feature of the side products is that these unnatural bases destabilize the double-stranded oligonucleotides in which they are incorporated, such that these synthetic failures melt at a lower temperature than synthetic double-stranded oligonucleotides containing only natural bases.

Denaturing conditions can be applied to a variety of methodologies used or adapted for preparative (rather than analytical) purposes, including chromatography. Column chromatography and gel chromatography are examples of suitable methodologies within the present invention. In one embodiment, the column chromatography is high performance liquid chromatography ("HPLC"). In another embodiment, the column chromatography uses a monolithic matrix as described by Hatch in U.S. Pat. No. 6,238,565. In another embodiment, the column chromatography is "Denaturing Anion-Exchange HPLC" (DEAHPLC) as described by Taylor in WO 01/27331 A2. In another embodiment, the column chromatography is Isocratic HPLC as described by Gjerde in U.S. Pat. No. 6,024,878. In another embodiment, the column chromatography is "Fully Denaturing HPLC" (FDHPLC). A preferred embodiment is use of a technique termed "denaturing HPLC" ("DHPLC"). In another embodiment, the chromatography is gradient gel chromatography. As used herein, denaturing conditions refer to both partially denaturing conditions under which oligonucleotides are partially denatured, and fully denaturing conditions under which oligonucleotides are fully denatured. Partially denaturing refers to the separation of a mismatched base pair in a double-stranded oligonucleotide while a portion or all of the remainder of the double strand remains intact. This occurs because a double strand will denature more easily (e.g., at a lower temperature) at the site of a base pair mismatch than is required to denature the remainder of the strand.

Oligonucleotides suitable for use in the present invention are any double-stranded sequence. Preferred oligonucleotides are double-stranded DNA. Double-stranded DNA includes full length genes and fragments of full length genes. For example, the DNA fragments may be portions of a gene that when joined form a larger portion of the gene or the entire gene.

The separation by DHPLC of synthetic double-stranded DNA fragments containing only natural bases, from synthesis side products is described as a representative example of the present invention. DHPLC is an analytical technique that has been used to detect mutations that occur in DNA isolated from natural sources. The technique detects polymorphisms in genomic DNA after PCR amplification. The technique is performed as follows. A test sample is formed by PCR amplifying the region of interest in the genomic DNA. This test sample is mixed with an amplified control sample obtained from DNA without a polymorhpism. This mixture of the test and control samples is denatured and renatured to form duplexes composed of amplified strands from both samples. This test mixture is then analyzed by DHPLC. Oefner and his colleagues have described two variations of DHPLC: the first in which the separation is done under partially denaturing conditions (Oefner, P. J., Underhill, P. A. (1998) Detection of Nucleic Acid Heteroduplex Molecules by Denaturing High-Performance Liquid Chromatography and Methods for Comparative Sequencing, U.S. Pat. No. 5,795,976, and Oefner, P. J., Underhill, P. A. (1998) DNA mutation detection using denaturing high-performance liquid chromatography, Current Protocols in Human Genetics, Wiley & Sons, N.Y., Supplement 19, 7.10.1–7.10.12) and a second version in which the DNA molecules are fully denatured (Oefner, J. Chromatogr. B. Biomed. Sci. Appl. 739(2):345–355, 2000). In the present invention, it was discovered that DHPLC can be used as a preparative technique to enrich a population synthetic DNA fragments for molecules which do not contain synthetic side products. Double-stranded DNA fragments in the 15 base pair to 10,000 base pair range are typically produced during chemical synthesis of large DNA fragments. Within the present invention, these intermediates are subjected to preparative DHPLC (using an automated system such as the ProStar Helix HPLC system from Varian Inc., Walnut Creek, Calif.) under conditions sufficient to isolate a population of high purity fragments of synthetic DNA and thus reduce the sequence error rate.

Each fragment is analyzed using software (e.g., DHPLC Melt Program, Stanford University, Palo Alto, Calif.; WAVEMAKER™ Utility Software, Transgenomic, Inc., Omaha, Nebr.; computer method described by Altshuler, U.S. Pat. No. 6,197,516) to calculate a specific run condition (e.g., temperature and gradient conditions) sufficient for depleting or initiating depletion of synthetic failures from the desired double-stranded oligonucleotide population. The fragments are injected onto the HPLC and run under the specified conditions. It will be evident to those of ordinary skill in the art that adjustments (e.g., a change of a few degrees of temperature) may be made to optimize the conditions for a particular fragment. The major peak is collected and dried down to remove solvents, then used to continue the assembly of the gene. Synthetic side products, for example, will fail to base pair with the intended complementary natural bases. DNA sequences containing side products will thus have a lowered melting point and show altered mobility under these conditions. The DNA molecules in the major peak all have the same melting profile and are less likely to carry synthetic side products.

DHPLC can be readily automated and can provide a high-throughput method of physically reducing synthetic side products from a chemically synthesized DNA sample. For example, synthetic DNA fragments of less than 1000 bp in length are injected onto the column under conditions that partially denature the DNA, the major peak collected and the remainder of the HPLC flow-through discarded. The peak contains the DNA fragment; most of the molecules in the original population which carry synthetic side-products in place of natural bases show altered mobility and thus will be discarded. Alternatively, synthetic DNA fragments of less than 100 bp in length are injected into the column under conditions that fully denature the DNA strands. The two major peaks are collected and the remainder of the HPLC flow-through discarded. Each of the two peaks contains one strand of the synthetic DNA; most of the molecules in the original population which carry synthetic side products instead of natural bases show altered mobility and thus will be discarded. The two peaks are combined and hybridized together to form an intermediate fragment for gene synthesis which is less likely to carry synthetic side products and is thus more likely to yield the desired sequence when it is cloned.

As mentioned above, the chromatography is performed under conditions appropriate to separatively deplete the synthetic failures from the desired double-stranded DNA. In one embodiment, the thermal and gradient conditions are adjusted to permit separation by DHPLC. The thermal and gradient conditions may be calculated using a DHPLC Melt Program available from Stanford University, Palo Alto, Calif. (http://insertion.stanford.edu/melt.html). Each double-stranded DNA denatures at a temperature that is a function of the strength of the duplex structure. A fully natural base paired DNA sequence forms the most stable duplex and denatures under the most stringent conditions. DNA sequences with base modifications form less stable duplexes, denature at a lower temperature and thus show increased mobility at a given temperature and gradient profile.

Gel based techniques such as double-stranded conformational analysis (DSCA) and capillary-based conformation-sensitive gel electrophoresis (capillary CSGE) can also be used to enrich the abundance of correct sequence in a population of nucleic acid sequences. Like DHPLC, these gel based methods are analytical techniques that have been used to detect mutations based upon the conformation in the double strand caused by a non-matching base pairs. These techniques rely on the differing electrophoretic mobility of a heteroduplex from the homoduplex. Several other mutation detection techniques based upon slab gels [e.g., constant gradient gel electrophoresis (CGGE), denaturing gradient gel electrophoresis (DGGE), and temperature gradient gel electrophoresis (TGGE)] are based on the subtle differences of melting points of DNA fragments dependent on base pair composition and the resultant difference of mobility of the mutant fragment in gels. The separated populations of double-stranded nucleic acids can be isolated by excision of bands from the gel.

Capillary CSGE is based upon capillary electrophoresis (Rozycka M, Collins N, Stratton M R, Wooster R., Genomics 70(1):34–40, 2000). Like DSCA, this technique relies on conformational differences between heteroduplex and homoduplex nucleic acids. For CSGE, fractions containing size or shape fractionated DNA fragments can be collected on moving affinity membranes or into sample chambers. The exact timing of the collection steps is achieved by determining the velocity of each individual zone measured between two detection points near the end of the capillary.

A preferred use of the present invention is for chemical gene synthesis by enriching fractions for double-stranded DNA fragments which contain only natural bases. Such fragments are joined (e.g., ligated) to form the complete gene.

The following examples are offered by way of illustration and not by way of limitation.

EXAMPLES

Example 1

Synthesis of a 205 BP DNA Fragment From the Operator-Binding Region of the LacI Gene Beta-galactosidase is an enzyme that can convert X-gal from a colorless compound into a brilliant blue compound (Manniatis; Sambrook et al., *Molecular Cloning: A Laboratory Manual*, Cold Spring Harbor Laboratories, Cold Spring Harbor, N.Y., 1989). The lacI gene encodes a repressor of beta-galactosidase synthesis in *E. coli*. In a cell with functional lac repressor, the synthesis of beta-galactosidase is suppressed and colonies grown on X-gal plates are white. If the lac repressor gene is inactive, beta-galactosidase is produced and the colonies are a bright blue color. Because the function of the lac repressor can be measured with simple, in vivo assays it has been the subject of extensive genetic analysis (Markiewicz et al., J. Mol. Biol. 240:421–33, 1994; Suckow, et al., J. Mol. Biol. 261:421–33 1996). Based on this work, four G residues in a 205 base pair fragment which can not be changed without inactivating the protein were chosen. The sequence at these residues can thus be determined by assaying for Lac repressor function.

A 205 base pair segment of the lad gene with the sequence (SEQ ID NO:1):

son (Muskegon, Mich.). Triethylammonium acetate (TEAA), pH 7.0, and 3% Trifluoroacetic acid in water are obtained from Glen Research. After purification, the synthesized oligonucleotides are evaporated to dryness in a SpeedVac (Savant, Farmingdale, N.Y.) and resuspended in HPLC grade water. Concentrations of the oligonucleotides are determined by reading the 260 nm absorbance on a Pharmacia LKB Ultrospec III (Amersham Pharmacia, Upsala, Sweden).

The oligonucleotides are used to form duplex fragments by drying 500 pmoles each of the complementary oligonucleotides in a speedvac and resuspending in 10 microliters TE. A 5 microliter sample of the solution (250 pmoles) is mixed with 10 microliters of 2×SSPE (prepared according to Manniatis), heated to 95° C. and cooled to room temperature.

Duplexes are successively ligated together to make longer fragments until the full length product is made. Each ligation consists of 500 picomoles of a pair of double-stranded oligonucleotide, 3 microliters of 10× ligation buffer (Fermentas Inc., Hanover, Md.), 10 units of T4 DNA ligase (product # EL0016, Fermentas) and water to make a total volume of 30 microliters. All duplexes are ligated together under the same conditions. Each ligation mix is incubated at 37° C. for 60 minutes, heated to 65° C. for 10 minutes and the fragment isolated by HPLC.

High performance liquid chromatography (HPLC) is performed on a ProStar Helix HPLC system from Varian Inc. (Walnut Creek, Calif.) consisting of two high-precision high-pressure pumps (ProStar 215 Solvent Delivery Modules), a column oven (ProStar 510 Air Oven), a UV detector (ProStar 320 UV/Vis Detector) and a fraction collector (Dynamax FC-1 Fraction Collector), all controlled by Star Chromatography Workstation Software (Version 5.31). The column used is a Zorbax Eclipse dsDNA Analysis Column (4.6 mm ID×75 mm, 3.5 micron) equipped with an in line Guard Column (4.6 mm ID×12.5 mm, 3.5 micron) both from Agilent Technologies, Inc. (Palo Alto, Calif.). The

```
  1 AATTCATAAA GGAGATATCA TATGAAACCG GTAACGTTAT ACGACGTCGC TGAATACGCC
 61 GGCGTTTCTT ACCAGACCGT TTCTAGAGTG GTTAACCAGG CTTCACATGT TAGCGCTAAA
121 ACCCGGGAAA AAGTTGAAGC TGCCATGGCT GAGCTCAACT ACATCCCGAA CCGTGTTGCG
181 CAGCAGCTGG CTGGTAAACA AAGCT
``` is synthesized using a set of overlapping double-stranded oligonucleotides.

The oligonucleotides used to make the gene are prepared using an Oligo 1000M DNA Synthesizer (Beckman Coulter, Inc, Fullerton, Calif.) using Beckman 30 nM DNA Synthesis Columns. All standard phosphoramidites and ancillary synthesis reagents are obtained from Glen Research, Inc. (Sterling, Va.). Chemical phosphorylation of the oligonucleotides is done with the Chemical Phosphorylation II (Glen Research). Concentrated ammonia is obtained from Fisher Scientific (Springfield, N.J.). 40% N-methylamine is obtained from Fluka Chemical Corporation (Milwaukee, Wis.). After cleavage from the solid support, the oligonucleotides are Trityl On purified using Poly-Pak Cartridges according to the instruction manual provided by Glen Research. Reagents for Trityl On purification are HPLC-grade acetonitrile and water obtained from Burdick & Jackfollowing pre-made buffers are obtained from Varian Inc. (Walnut Creek, Calif.); Helix BufferPak "A" (100 mM Triethylammonium acetate, pH 7.0, 0.1 mM EDTA) and Helix BufferPak "B" (100 mM Triethylammonium acetate, pH 7.0, 0.1 mM EDTA with 25% by volume acetonitrile). The thermal and gradient conditions for isolating chemically-pure enriched sequence are calculated using the DHPLC Melt Program (http://insertion.stanford.edu/melt.html) available from Stanford University (Palo Alto, Calif.). Elution profiles are monitored using UV detector with absorbance at 260 nm.

The ligated fragments are dried down from the HPLC buffer and resuspended in TE. These fragments are used in a second set of ligation reactions. Several rounds of ligation followed by purification and fragment isolation are used to build the 205 base pair fragment of the lacI gene.

Example 2

Functional Testing of the 205 Base Pair Fragment of the LacI Gene

The synthetic fragment produced in Example 1 is cloned into the lacI gene to test its function. Three micrograms of plasmid vector pWB1000 (Lehming et al., PNAS, 85:7947–7951, 1988) is digested with restriction enzymes EcoR1 and HindIII and the vector fragment gel purified using a Strata Prep DNA extraction kit (Stratagene product#400766) according to the manufacturers instructions, and resuspended in 100 microliters of TE. One microgram of the lacI fragment is treated with T4 polynucleotide kinase, extracted once with phenol and once with chloroform, ethanol precipitated and resuspended in 20 microliters of TE. Five microliters of the cut vector and one microliter of the synthetic lacI fragment are ligated in a total volume of 100 microliters using Fermentas T4 DNA ligase according to the manufacturers instructions. The ligation mix is extracted once with Strataclean, concentrated and washed twice with $1/10^{th}$ concentration TE and brought to a volume of 10 microliters in $1/10^{th}$ concentration TE. One microliter of this mix is transferred into E. coli strain DC 41-2 carrying plasmid pWB310 (Lehming et al., EMBO 6:3145–3153, 1987) by electroporation using a BTX ECM399 electroporator (Genetronics, Inc., San Diego, Calif.) according to the manufacturers instructions. Colonies were grown overnight on LB plates in the presence of 10 mg/liter tetracycline, 200 mg/liter ampicillin, 60 mg/liter X-gal and 300 mg/liter IPTG. Colonies carrying a plasmid with a functional lacI gene are white; those without a functional lacI gene are blue.

Example 3

Preparation of 205 BP DNA Fragments Containing Diaminopurine at Bases 86, 88, 133, or 178

One common side reaction of oligonucleotide synthesis is the formation of diaminopurine from a dG residue in the DNA chain. Modified oligonucleotides containing 2,6-diaminopurine are obtained from Trilink Biotechnologies (San Diego, Calif.) and incorporated into the 205 bp lacI gene fragment. Four samples were prepared as described in Example 1, with one diaminopurine residue (labeled D below) substituted for a dG residue in each sample.

| Oligonucleotide | Fragment Name | Base Replaced | SEQ ID NO: |
|---|---|---|---|
| 5' ACCGTTTCTADAGTGGTTAACCAGG 3' | D-T86 | 86 | 2 |
| 5' ACCGTTTCTAGADTGGTTAACCAGG 3' | D-T88 | 88 | 3 |
| 5' GGAAAAADTTGAAGCTGCCATGGCT 3' | D-T133 | 133 | 4 |
| 5' TTDCGCAGCAGCTGGCTGGTAAACAA 3' | D-T178 | 178 | 5 |

Example 4

Preparation of 205 BP DNA Fragments Containing a DU at Positions 86 or 133

A second common side reaction of oligonucleotide synthesis is deamination of the N4-amine of deoxycytidine to form a uracil (dU) in the DNA chain. Modified oligonucleotides containing uracil (dU) are obtained from Midland Certified Reagent Company (Midland, Tex.) and incorporated into the 205 bp lad gene fragment. Two samples were prepared as described in Example 1, with one uracil residue (labeled dU below) substituted for a dC residue in each sample.

| Oligonucleotide | Fragment Name | Base Replaced | SEQ ID NO: |
|---|---|---|---|
| 5' TGAAGCCTGGTTAACCACTdUTAGAA 3' | U-B86 | 86 | 6 |
| 5' AGCTCAGCCATGGCAGCTTCAAdUTT 3' | U-B133 | 133 | 7 |

Example 5

Preparation of 205 BP DNA Fragments Containing an Abasic Site at Positions 134 or 182

A third common side reaction of oligonucleotide synthesis is the formation of abasic sites by depurination of protected adenosine residues during chain elongation. Modified oligonucleotides containing uracil are obtained from Midland Certified Reagent Company (Midland, Tex.) and incorporated into the 205 bp lad gene fragment. Two samples were prepared as described in Example 1, with one uracil residue (labeled dU below) substituted for a dA residue in each sample.

| Oligonucleotide | Fragment Name | Base Replaced | SEQ ID NO: |
|---|---|---|---|
| 5' AGCTCAGCCATGGCAGCTTCAdUCTT 3' | A-B134 | 134 | 8 |
| 5' TTGCGCdUGCAGCTGGCTGGTAAACAA 3' | A-T182 | 182 | 9 |

After synthesis and HPLC purification of the 205 base pair fragments, the DNA is treated with Uracil-N-Glycosylase (Epicentre Technologies Corp., Madison, Wis.) according to the manufacturers instructions to remove the uracil base, leaving an apurinic site in place of the corresponding A residue in the native 205 base pair fragment.

Example 6

Calculation of Thermal and Gradient HPLC Conditions for LacI Sequence

The thermal and gradient conditions for isolating chemically-pure enriched sequence are calculated using the DHPLC Melt Program (http://insertion.stanford.edWmelt.html) available from Stanford University (Palo Alto, Calif.) and available for license from the Stanford University Office of Technology Licensing referring to the docket number S95-024. The 4 base single-stranded region on either end of the 205 base pair fragment is removed to give the following 197 base pair sequence (SEQ ID NO: 10).

lac I Region

CATAAAGGAGATATCATATGAAACCGGTAACGTTATACGACGTCGCTCAA

TACGCCGGCGTTTCTTACCAGACCGTTTCTAGAGTGGTTAACCAGGCTTC

ACATGTTAGCGCTAAAACCCGGGAAAAAGTTGAAGCTGCCATGGCTGAGC

TCAACTACATCCCGAACCGTGTTGCGCAGCAGCTGGCTGGTAAACAA

The gradients are specified below as percent buffer B at times 1, 2 and 3 (B1, B2, B3). The gradient is run from B1 to B2 in 0.5 minutes, then B2 to B3 in 3.0 minutes.

| Conditions | Temperature (C.) | B1 | B2 | B3 |
|---|---|---|---|---|
| 1 | 53 | 50 | 59.6 | 65 |
| 2 | 55 | 50 | 56.8 | 62.2 |
| 3 | 57 | 50 | 54.1 | 59.5 |
| 4 | 59 | 50 | 51.4 | 56.8 |
| 5 | 61 | 45 | 50 | 55.4 |

Buffer A and buffer B are as described in Example 1.

Example 7

Determination of the Temperature-dependent Chromatorgraphic Profiles of the Native and Eight Modified LacI Fragments The chromatographic behavior of the native lacI DNA and the eight modified lacI are measured in response to a range of gradient and temperature conditions DNA is below:

| Name | Type and Location of Modification |
|---|---|
| Pure | No chemical modification |
| D-T86 | 2,6-diaminopurine @ position 86 |
| D-T88 | 2,6-diaminopurine @ position 88 |
| D-T133 | 2,6-diaminopurine @ position 133 |
| D-T178 | 2,6-diaminopurine @ position 178 |
| U-B86 | 2'-deoxyuridine @ position 79 |
| U-B133 | 2'-deoxyuridine @ position 133 |
| A-B134 | abasic @ position 134 |
| A-T182 | abasic @ position 182 |

25 pmoles of each sample is suspended in 5 μl of HPLC-grade water and directly chromatographed on a Zorbax Eclipse ds DNA Analysis Column (4.6 mm ID×75 mm, 3.5 micron) with an in line Pre-Column (4.6 mm ID×12.5 mm, 3.5 micron) with Buffer A consisting of 100 mM Triethylammonium acetate, pH 7.0, 0.1 mM EDTA and Buffer B consisting of 100 mM Triethylammonium acetate, pH 7.0, 0.1 mM EDTA with 25% by volume acetonitrile. The details of each gradient and temperature condition are as described in Example 6.

Each fragment denatures at a temperature that is a function of the strength of the duplex structure. The fully base paired native lacI sequence forms the most stable duplex and denatures under the most stringent conditions. Fragments with base modifications form less stable duplexes, denature at a lower temperature and thus show earlier elution at a given temperature and gradient profile.

Example 8

Functional Testing of 205 Base Pair Fragments of the LacI Gene Carrying Modified Bases The synthetic fragments produced in Example 3, Example 4 and Example 5 (fragments D-T86, D-T88, D-T133, D-T178, U-B86, U-B133, A-B134, A-T182) are cloned into the lacI gene to test their biological function. Ten micrograms of plasmid vector pWB1000 (Lehming et al., PNAS 85:7947–7951, 1988) is digested with restriction enzymes EcoR1 and HindIII and the vector fragment gel purified using a Strata Prep DNA extraction kit (Stratagene product #400766) according to the manufacturers instructions, and resuspended in 100 microliters of TE. One microgram of each lacI fragment is treated with T4 polynucleotide kinase, extracted once with phenol and once with chloroform, ethanol precipitated and resuspended in 20 microliters of TE. Five microliters of the cut vector and one microliter of the synthetic lacI fragment are ligated in a total volume of 100 microliters using New England Biolabs T4 DNA ligase according to the manufacturers instructions. The ligation mix is extracted once with Strataclean, concentrated and washed twice with $\frac{1}{10}^{th}$ concentration TE and brought to a volume of 10 microliters in $\frac{1}{10}^{th}$ concentration TE. One microliter of this mix is transferred into E. coli strain DC 41-2 carrying plasmid pWB310 (Lehming et al., EMBO 6:3145–3153, 1987) by electroporation using a BTX ECM399 electroporator according to the manufacturers instructions. Colonies are grown overnight on LB plates in the presence of 10 mg/liter tetracycline, 200 mg/liter ampicillin, 60 mg/liter X-gal and 300 mg/liter IPTG. Colonies carrying a plasmid with a functional lacI gene are white; those without a functional lacI gene are blue. Each modified fragment is characterized by the frequency of blue colonies relative to the frequency of blue colonies derived from clones of the native synthetic lacI fragment as described in Example 2.

Example 9

Enrichment of Native LacI Fragments from Mixtures of Native and Modified LacI Fragments by Preparative HPLC The ability of the HPLC technique to enrich "correct" synthetic DNA in the presence of synthetic DNA containing side product is shown by spiking native lacI DNA with each of the eight modified lacI DNA and enriching for the native DNA from the mixture using HPLC. For each of the eight modified DNA fragments (fragments D-T86, D-T88, D-T133, D-T178, U-B86, U-B133, A-B134, A-T182) an equimolar mixture is prepared of native and modified fragments by mixing 20 pmoles of the modified fragment with 20 pmoles of the native fragment. A fraction of each mixture is retained for functional testing as described below. The remainder of each of these samples is chromatographed using thermal and gradient conditions (identified in Example 7) which alter the mobility of the modified fragments relative to the native fragment. For each sample, the peaks are collected with a fraction collector as described in Example 1 at the elution time determined in Example 7. Two fractions are collected, one with a mobility characteristic of the modified DNA fragments and one with a slower mobility characteristic of the native DNA fragment. These fractions are dried down and cloned as described in Example 8. In parallel, a portion of each of the eight unfractionated mixtures is cloned and tested in the same way. The "native fraction" fragments show a lower number of sequence errors than the original mixtures or the early-eluting fractions, as indicated by the frequency of blue colonies.

Example 10

Preparation of 48 BP Double-stranded Fragments Containing N−1, N+, T/G and G/G Synthetic Errors The ability of HPLC to separate "correct" synthetic DNA from DNA containing synthetic errors such as mismatches caused by ligation or n−1 and n+ side products formed during chemical oligonucleotide synthesis is shown by spiking the correct sequence 48 bp double-stranded control with each of the four modified 48 mers. Each of the 48 bp double-stranded nucleic acids is synthesized using a set of overlapping double-stranded oligonucleotides.

The control and the four sequences containing the synthesis byproducts are listed below:

Example 11

Calculation of Thermal of Gradient HPLC Conditions for the 48 Mer Sequence

The thermal and gradient conditions for isolating chemically-pure enriched sequence are calculated using the DHPLC Melt Program. The control sequence in Example 10 was used as the input for the calculation.

The gradient is specified below as percent buffer B. The gradient is run from B1 to B2 in 0.5 minutes, then B2 to B3 in 3.0 minutes.

| Temperature (C.) | B1 | B2 | B3 |
|---|---|---|---|
| 62 | 40.2 | 45.2 | 50.6 |

Buffer A and buffer B are as described in Example 1.

Example 12

Separation by Preparative HPLC of a Correct 48 BP Double-stranded Control Fragment from 48 BP Double-stranded Fragments Containing N−1, N+, T/G AND G/G Synthetic Errors The control fragment and a 1:1 mixture of the control fragment with each of the fragments containing synthetic errors are subjected to HPLC. A 12.5 pmol sample is used for the control and 25 pmoles (12.5 pmol of the control+12.5 pmol of the error containing fragment) of each mixed sample are suspended in 5 µl of HPLC-grade water and directly chromatographed on a Zorbax Eclipse ds DNA Analysis Column (4.6 mm ID×75 mm, 3.5 micron) with an in line Pre-Column (4.6 mm ID×12.5 mm, 3.5 micron) with Buffer A consisting of 100 mM Triethylammonium acetate, pH 7.0, 0.1 mM EDTA and Buffer B consisting of 100 mM Triethylammonium acetate, pH 7.0, 0.1 mM EDTA with 25% by volume acetonitrile. The details of the gradient and temperature conditions are as described in Example 11.

Under the HPLC conditions used, the control fragment elutes as a single peak. For each of the four separations of the mixtures of the control fragment with a fragment containing synthetic errors, a peak with at least as much area under the curve of the control peak, elutes with a retention time corresponding to the control peak. New peaks eluting at earlier times than the control peak are present in each of the chromatograms of the mixtures.

Each of the peaks from above is collected by the fraction collector described in Example 1. These fractions are evaporated and resuspended into 100 uL of water. 5 uL of these samples are reinjected into the HPLC using the same conditions as described above. The retention time for each peak remains the same.

The HPLC conditions used separate the mixtures into a population with a retention time corresponding to the control and into a population different from the control.

From the foregoing, it will be evident that, although specific embodiments of the invention have been described herein for purposes of illustration, various modifications may be made without deviating from the spirit and scope of the invention.

```
5'-ATTCGCCCTTTGCCACTAAGCACCAGCGAAACGGTACTTACCGACACG-3'   Control        (SEQ ID NO:11)

5'-ATTCGCCCTTTGCCACTAAGCACCAGCGAAACGGTACT_ACCGACACG-3'   n-1            (SEQ ID NO:12)

5'-ATTCGCCCTTTGCCACTAAGCACCAGCGAAACGGTACTTTACCGACACG-3'  n+             (SEQ ID NO:13)

5'-ATTCGCCCTTTGCCACTAAGCACCAGCGAAACGGTACTTGCCGACACG-3'   T/G Mismatch   (SEQ ID NO:14)

5'-ATTCGCCCTTTGCCACTAAGCACCAGCGAAACGGTACTTAGCGACACG-3'   G/G Mismatch   (SEQ ID NO:15)
```

What is claimed is:

1. A method for improving the sequence fidelity of synthetic double-stranded oligonucleotides, comprising subjecting synthetic double-stranded oligonucleotides to preparative high performance liquid chromatography (HPLC) under partially denaturing conditions sufficient to separate synthetic double-stranded oligonucleotides into two populations of which one population is enriched for synthetic failures and the other population is depleted of synthetic failures.

2. A method according to claim 1, wherein the chromatography is denaturing high performance liquid chromatography (DHPLC).

3. A method according to claim 1 or claim 2, wherein the oligonucleotides comprise synthetic double-stranded DNA.

4. A method according to claim 3, wherein the DNA comprises one or more fragments of a gene.

5. A method according to claim 1 or claim 2, wherein the synthetic failures separated are molecules containing a uridine, apurinic, apyrimidinic or diaminopurine residue.

6. A method according to claim 1 or claim 2, wherein the double-stranded oligonucleotides are synthesized chemically.

7. A method according to claim 6, wherein the oligonucleotides comprise double-stranded DNA.

8. A method according to claim 7, wherein the DNA comprises one or more fragments of a gene.

9. A method according to claim 3, further comprising joining oligonucleotides from the population depleted of synthetic failures, to other synthetic oligonucleotides.

10. A method according to claim 9, wherein a gene or gene fragment is formed when the oligonucleotides are joined.

11. A method according to claim 7, further comprising joining oligonucleotides from the population depleted of synthetic failures, to other synthetic oligonucleotides.

12. A method according to claim 11, wherein a gene or gene fragment is formed when the oligonucleotides are joined.

* * * * *